(12) United States Patent
Green et al.

(10) Patent No.: US 11,060,146 B2
(45) Date of Patent: Jul. 13, 2021

(54) METHOD AND KIT FOR IDENTIFYING GENE MUTATIONS

(71) Applicant: UNIVERSITY OF PRETORIA, Pretoria (ZA)

(72) Inventors: Robin John Green, Sandton (ZA); Refiloe Masekela, Durban (ZA); Cheryl Stewart, Pretoria (ZA); Michael Sean Pepper, Pretoria (ZA)

(73) Assignee: UNIVERSITY OF PRETORIA, Pretoria (ZA)

(*) Notice: Subject to any disclaimer, the term of this patent is extended or adjusted under 35 U.S.C. 154(b) by 221 days.

(21) Appl. No.: 15/773,800

(22) PCT Filed: Nov. 3, 2016

(86) PCT No.: PCT/IB2016/056606
§ 371 (c)(1),
(2) Date: May 4, 2018

(87) PCT Pub. No.: WO2017/077471
PCT Pub. Date: May 11, 2017

(65) Prior Publication Data
US 2018/0320231 A1   Nov. 8, 2018

(30) Foreign Application Priority Data
Nov. 4, 2015 (GB) .................................. 1519501

(51) Int. Cl.
*C12Q 1/6883* (2018.01)
*G16B 30/00* (2019.01)

(52) U.S. Cl.
CPC .......... *C12Q 1/6883* (2013.01); *G16B 30/00* (2019.02); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2003/0008281 | A1  | 1/2003  | Weston et al. |
| 2004/0096844 | A1* | 5/2004  | Accola ............... C12Q 1/6883 435/6.12 |
| 2008/0153088 | A1* | 6/2008  | Sun .................... C12Q 1/6883 435/6.11 |
| 2014/0302501 | A1  | 10/2014 | Xu et al. |

OTHER PUBLICATIONS

McGinniss (Hum Genet 2005 vol. 118 pp. 331-338).*
NEB catalog (1998/1999 pp. 121,284).*
Rowntree (Annals of Human Genetics vol. 67 Issue 5 pp. 471-485 Sep. 2003).*

* cited by examiner

*Primary Examiner* — Amanda Haney
(74) *Attorney, Agent, or Firm* — Saliwanchik, Lloyd & Eisenschenk

(57) ABSTRACT

This invention relates to a method of identifying mutations in the cystic fibrosis transmembrane conductance regulator (CFTR) gene, a kit for performing the method, and furthermore to isolated nucleotide sequences being complementary to one or more mutations of the CFTR gene. According to a first aspect of the invention there is provided a method of identifying mutations in the cystic fibrosis transmembrane conductance regulator (CFTR) gene, including the steps of providing one or more nucleic acid sequences, fully complementary to one or more segments of the CFTR gene, wherein the one or more nucleic acid sequences correspond to the mutation to be identified; providing a biological sample of an individual to be tested for CF; isolating nucleic acids from the biological sample; and testing the biological sample for the presence of one or more of the nucleic acid sequences using a suitable detection method.

20 Claims, No Drawings
Specification includes a Sequence Listing.

SEQUENCE LISTING

<160> NUMBER OF SEQ ID NOS: 36

<210> SEQ ID NO 1
<211> LENGTH: 53
<212> TYPE: DNA
<213> ORGANISM: Homo sapiens

<400> SEQUENCE: 1
aatagaaaaa cttctaatgg tgatgataca gcctcttctt cagtaatttc tca        53

<210> SEQ ID NO 2
<211> LENGTH: 119
<212> TYPE: DNA
<213> ORGANISM: Homo sapiens

<400> SEQUENCE: 2
ggaggaatag gtgaagatgt tagaaaaaaa atcaactgtg tcttgttcca ttccaggtgg   60 ctgcttttg gttgtgctgt ggctccttgg aaagtgagta ttccatgtcc tattgtgta   119

<210> SEQ ID NO 3
<211> LENGTH: 110
<212> TYPE: DNA
<213> ORGANISM: Homo sapiens

<400> SEQUENCE: 3
agatgcgatc tgtgagccga gtctttaagt tcattgacat gccaacagaa cagaaggtaa   60
acctaccaag tcaaccaaac catacaagaa tggccaactc tcgaaagtta              110

<210> SEQ ID NO 4
<211> LENGTH: 29
<212> TYPE: DNA
<213> ORGANISM: Artificial Sequence
<220> FEATURE:

```
<223> OTHER INFORMATION: tetra-ARMS primer

<400> SEQUENCE: 4
acaatagaaa aacttctaat ggtgataac                                    29

<210> SEQ ID NO 5
<211> LENGTH: 27
<212> TYPE: DNA
<213> ORGANISM: Artificial Sequence
<220> FEATURE:
<223> OTHER INFORMATION: tetra-ARMS primer

<400> SEQUENCE: 5
gagaaattac tgaagaagag gctgatt                                      27

<210> SEQ ID NO 6
<211> LENGTH: 28
<212> TYPE: DNA
<213> ORGANISM: Artificial Sequence
<220> FEATURE:
<223> OTHER INFORMATION: tetra-ARMS primer

<400> SEQUENCE: 6
cagtgtaatg gatcatgggc catgtgct                                     28

<210> SEQ ID NO 7
<211> LENGTH: 27
<212> TYPE: DNA
<213> ORGANISM: Artificial Sequence
<220> FEATURE:
<223> OTHER INFORMATION: tetra-ARMS primer

<400> SEQUENCE: 7
gctcgccatg tgcaagatac agtgttg                                      27

<210> SEQ ID NO 8
<211> LENGTH: 20
<212> TYPE: DNA
<213> ORGANISM: Artificial Sequence
<220> FEATURE:
<223> OTHER INFORMATION: tetra-ARMS primer

<400> SEQUENCE: 8
ccattccagg tggctgcctc                                              20

<210> SEQ ID NO 9
<211> LENGTH: 21
<212> TYPE: DNA
<213> ORGANISM: Artificial Sequence
<220> FEATURE:
<223> OTHER INFORMATION: tetra-ARMS primer

<400> SEQUENCE: 9
ggagccacag cacaaccaca a                                            21

<210> SEQ ID NO 10
<211> LENGTH: 27
<212> TYPE: DNA
<213> ORGANISM: Artificial Sequence
<220> FEATURE:
<223> OTHER INFORMATION: tetra-ARMS primer

<400> SEQUENCE: 10
ctgctggacc caggaacaaa gcaaagg                                      27
```

```
<210> SEQ ID NO 11
<211> LENGTH: 29
<212> TYPE: DNA
<213> ORGANISM: Artificial Sequence
<220> FEATURE:
<223> OTHER INFORMATION: tetra-ARMS primer

<400> SEQUENCE: 11
cactatattg tccaggctgg agtgcggtg                                    29

<210> SEQ ID NO 12
<211> LENGTH: 22
<212> TYPE: DNA
<213> ORGANISM: Artificial Sequence
<220> FEATURE:
<223> OTHER INFORMATION: tetra-ARMS primer

<400> SEQUENCE: 12
ttcattgaca tgccaacagt ag                                           22

<210> SEQ ID NO 13
<211> LENGTH: 24
<212> TYPE: DNA
<213> ORGANISM: Artificial Sequence
<220> FEATURE:
<223> OTHER INFORMATION: tetra-ARMS primer

<400> SEQUENCE: 13
ggtaggttta ccttctgttc tgtt                                         24

<210> SEQ ID NO 14
<211> LENGTH: 29
<212> TYPE: DNA
<213> ORGANISM: Artificial Sequence
<220> FEATURE:
<223> OTHER INFORMATION: tetra-ARMS primer

<400> SEQUENCE: 14
gaatcttcag tagtggtttt gaggtgtgg                                    29

<210> SEQ ID NO 15
<211> LENGTH: 27
<212> TYPE: DNA
<213> ORGANISM: Artificial Sequence
<220> FEATURE:
<223> OTHER INFORMATION: tetra-ARMS primer

<400> SEQUENCE: 15
tgctaacaca ttgctcaggc tactggg                                      27

<210> SEQ ID NO 16
<211> LENGTH: 30
<212> TYPE: DNA
<213> ORGANISM: Artificial Sequence
<220> FEATURE:
<223> OTHER INFORMATION: qPCR probe

<400> SEQUENCE: 16
gtgtgttttt ttaacaggga tttggggaat                                   30

<210> SEQ ID NO 17
<211> LENGTH: 24
<212> TYPE: DNA
<213> ORGANISM: Artificial Sequence
<220> FEATURE:
<223> OTHER INFORMATION: qPCR probe
```

```
<400> SEQUENCE: 17
ggatccagca accgccaaca actg                                          24

<210> SEQ ID NO 18
<211> LENGTH: 27
<212> TYPE: DNA
<213> ORGANISM: Artificial Sequence
<220> FEATURE:
<223> OTHER INFORMATION: qPCR probe

<400> SEQUENCE: 18
atgtgaattt agatgtgggc atgggag                                       27

<210> SEQ ID NO 19
<211> LENGTH: 27
<212> TYPE: DNA
<213> ORGANISM: Artificial Sequence
<220> FEATURE:
<223> OTHER INFORMATION: qPCR probe

<400> SEQUENCE: 19
tctttccact accataatgc ttgggag                                       27

<210> SEQ ID NO 20
<211> LENGTH: 29
<212> TYPE: DNA
<213> ORGANISM: Artificial Sequence
<220> FEATURE:
<223> OTHER INFORMATION: qPCR probe

<400> SEQUENCE: 20
gcccgacaaa taaccaagtg acaaatagc                                     29

<210> SEQ ID NO 21
<211> LENGTH: 26
<212> TYPE: DNA
<213> ORGANISM: Artificial Sequence
<220> FEATURE:
<223> OTHER INFORMATION: qPCR probe

<400> SEQUENCE: 21
agggccagat gtcatctttc ttcacg                                        26

<210> SEQ ID NO 22
<211> LENGTH: 22
<212> TYPE: DNA
<213> ORGANISM: Artificial Sequence
<220> FEATURE:
<223> OTHER INFORMATION: qPCR primer

<400> SEQUENCE: 22
atgggccatg tgcttttcaa ac                                            22

<210> SEQ ID NO 23
<211> LENGTH: 20
<212> TYPE: DNA
<213> ORGANISM: Artificial Sequence
<220> FEATURE:
<223> OTHER INFORMATION: qPCR primer

<400> SEQUENCE: 23
gcaaccgcca acaactgtcc                                               20

<210> SEQ ID NO 24
<211> LENGTH: 20
```

-continued

<212> TYPE: DNA
<213> ORGANISM: Artificial Sequence
<220> FEATURE:
<223> OTHER INFORMATION: qPCR primer

<400> SEQUENCE: 24
tagatgtggg catgggagga                               20

<210> SEQ ID NO 25
<211> LENGTH: 23
<212> TYPE: DNA
<213> ORGANISM: Artificial Sequence
<220> FEATURE:
<223> OTHER INFORMATION: qPCR primer

<400> SEQUENCE: 25
ccactaccat aatgcttggg aga                           23

<210> SEQ ID NO 26
<211> LENGTH: 22
<212> TYPE: DNA
<213> ORGANISM: Artificial Sequence
<220> FEATURE:
<223> OTHER INFORMATION: qPCR primer

<400> SEQUENCE: 26
gcccgacaaa taaccaagtg ac                            22

<210> SEQ ID NO 27
<211> LENGTH: 19
<212> TYPE: DNA
<213> ORGANISM: Artificial Sequence
<220> FEATURE:
<223> OTHER INFORMATION: qPCR primer

<400> SEQUENCE: 27
acagtcattt ggccccctg                                19

<210> SEQ ID NO 28
<211> LENGTH: 32
<212> TYPE: DNA
<213> ORGANISM: Artificial Sequence
<220> FEATURE:
<223> OTHER INFORMATION: qPCR hybprobe

<400> SEQUENCE: 28
tgatgaatca gcctcttctt cagtaatttc tc                 32

<210> SEQ ID NO 29
<211> LENGTH: 35
<212> TYPE: DNA
<213> ORGANISM: Artificial Sequence
<220> FEATURE:
<223> OTHER INFORMATION: qPCR hybprobe

<400> SEQUENCE: 29
acttcttggt actcctgtcc tgaaagatat taatt              35

<210> SEQ ID NO 30
<211> LENGTH: 24
<212> TYPE: DNA
<213> ORGANISM: Artificial Sequence
<220> FEATURE:
<223> OTHER INFORMATION: qPCR hybprobe

<400> SEQUENCE: 30

| | |
|---|---|
| tttttggttg tgctgtggct cctt | 24 |

<210> SEQ ID NO 31
<211> LENGTH: 32
<212> TYPE: DNA
<213> ORGANISM: Artificial Sequence
<220> FEATURE:
<223> OTHER INFORMATION: qPCR hybprobe

<400> SEQUENCE: 31

| | |
|---|---|
| ggaaagtgag tattccatgt cctattgtgt ag | 32 |

<210> SEQ ID NO 32
<211> LENGTH: 31
<212> TYPE: DNA
<213> ORGANISM: Artificial Sequence
<220> FEATURE:
<223> OTHER INFORMATION: qPCR hybprobe

<400> SEQUENCE: 32

| | |
|---|---|
| gccaacagaa cagaaggtaa acctaccaag t | 31 |

<210> SEQ ID NO 33
<211> LENGTH: 27
<212> TYPE: DNA
<213> ORGANISM: Artificial Sequence
<220> FEATURE:
<223> OTHER INFORMATION: qPCR hybprobe

<400> SEQUENCE: 33

| | |
|---|---|
| caaccaaacc atacaagaat ggccaac | 27 |

<210> SEQ ID NO 34
<211> LENGTH: 25
<212> TYPE: DNA
<213> ORGANISM: Artificial Sequence
<220> FEATURE:
<223> OTHER INFORMATION: microarray probe

<400> SEQUENCE: 34

| | |
|---|---|
| atggtgatga atcagcctct tcttc | 25 |

<210> SEQ ID NO 35
<211> LENGTH: 25
<212> TYPE: DNA
<213> ORGANISM: Artificial Sequence
<220> FEATURE:
<223> OTHER INFORMATION: microarray probe

<400> SEQUENCE: 35

| | |
|---|---|
| aggtggctgc tttttggttg tgctg | 25 |

<210> SEQ ID NO 36
<211> LENGTH: 25
<212> TYPE: DNA
<213> ORGANISM: Artificial Sequence
<220> FEATURE:
<223> OTHER INFORMATION: microarray probe

<400> SEQUENCE: 36

| | |
|---|---|
| acatgccaac agaacagaag gtaaa | 25 |

METHOD AND KIT FOR IDENTIFYING GENE MUTATIONS

CROSS REFERENCE TO RELATED APPLICATIONS

This application is a National Stage Application of International Application Number PCT/IB2016/056606, filed Nov. 3, 2016; which claims priority to Great Britain Application No. 1519501.9, filed Nov. 4, 2015.

The Sequence Listing for this application is labeled "SeqList-04May18-ST25.txt", which was created on May 4, 2018, and is 7 KB. The entire content is incorporated herein by reference in its entirety.

FIELD OF THE INVENTION

This invention relates to a method of identifying mutations in the cystic fibrosis transmembrane conductance regulator (CFTR) gene, a kit for performing said method, and furthermore to isolated nucleotide sequences being complementary to one or more mutations of the CFTR gene. More particularly, but not exclusively, the invention relates to a method and kit identifying mutations in the cystic fibrosis transmembrane conductance regulator (CFTR) gene in respect of patients of African origin, and specifically black and mixed raced patients.

BACKGROUND TO THE INVENTION

Cystic fibrosis (CF) is the most common, potentially lethal autosomal recessive disease among individuals of Caucasian descent in the world. CF is caused by mutations in the cystic fibrosis transmembrane conductance regulator (CFTR) gene, an ion channel protein primarily responsible for the trans-epithelial conductance of chloride ions. Dysfunctions in this protein lead to various symptoms being observed in CF patients, with the most common being the so called classic triad of CF symptoms, being elevated sweat chloride concentration, pancreatic insufficiency and chronic pulmonary disease, although this classic triad does not necessarily present in all CF patients, which could lead to misdiagnosis. Associated CF symptoms include failure to thrive, male infertility and microbial colonisation of the airway.

Whilst CF amongst patients of Caucasian descent has been studied and documented relatively extensively, CF is not limited to this demographic group, and has been identified in blacks and individuals of mixed race ancestry. This bias has affected diagnosis of, and research in, non-white patients, because of the underlying assumption that this disease could not affect other racial groups. As a result, European populations tend to have the highest rates of mutation detection and molecular diagnosis.

Literature indicates that CF patients from African (black and mixed race) ancestry are at a distinct disadvantage when compared to their European counterparts. The data suggests that the number of CF causing mutations in patients of European descent may be approaching a plateau, while the opposite is true for African CF patients.

There are two major challenges to diagnosing CF in African CF patients. First, they have a relatively rare disease which occurs at lower frequencies than those seen in patients of European descent. This may increase their chances of being misdiagnosed especially in areas where there are more rampant phenocopic illnesses such as malnutrition, viral or parasitic infection or tuberculosis. Second, there is not enough information available for the design of Afro-centric genetic tests. This increases the probability of misdiagnosis particularly if the patients don't present with the classic triad of CF symptoms or if they have milder forms of the disease. It is therefore important to cease the exclusion of CF as a diagnosis based on race.

U.S. Pat. No. 8,338,578 describes novel mutations of the CFTR gene related to CF or to conditions associated with CF, and further to probes for detecting mutant CFTR sequences, and methods of identifying said mutations of the CFTR gene in the genotype of an individual. However, it alludes to CF being the most common severe autosomal recessive genetic disorder in the Caucasian population, adding to the common misconception that CF does not affect patients of black and mixed race ethnic origins.

OBJECT OF THE INVENTION

It is accordingly an object of the invention to provide a method for identifying mutations in the cystic fibrosis transmembrane conductance regulator (CFTR) gene in respect of patients of African origin, and in particular black and mixed race patients, but without limiting the method to only these groups of patients, and a diagnostic kit for performing said method.

SUMMARY OF THE INVENTION

According to a first aspect of the invention there is provided a method of identifying mutations in the cystic fibrosis transmembrane conductance regulator (CFTR) gene, including the steps of:
   providing one or more nucleic acid sequences, fully complementary to one or more segments of the CFTR gene, wherein the said one or more nucleic acid sequences correspond to the mutation to be identified and may be selected from the group comprising SEQ ID: 1-3;
   providing a biological sample of an individual to be tested for CF;
   isolating nucleic acids from the biological sample; and
   testing the biological sample for the presence of one or more of the nucleic acid sequences using a suitable detection method.

The biological sample may be any sample obtained from the individual's blood, serum, plasma, urine, skin, hair or any other biological sample containing DNA.

Further according to a first aspect of the invention, the detection method may be one or more methods selected from the group consisting of an amplification refractory mutation system (ARMS), next generation sequencing (NGS), quantitative polymerase chain reaction (qPCR) and microarrays.

Still further according to a first aspect of the invention, the ARMS detection method may comprise one or more tetra-ARMS primers selected from the group consisting of SEQ ID: 4-15. The NGS detection method may comprise one or more probes selected from the group consisting of SEQ ID: 16-21. The qPCR detection method may comprise one or more primers and probes selected from the group consisting of SEQ ID: 22-27, as well as the corresponding hybprobes selected from the group consisting of SEQ ID: 28-33. The microarray detection method may comprise one or more probes selected from the group consisting of SEQ ID: 34-36.

Yet further according to the invention, the individual may be of African origin, and may more specifically be a black or mixed raced individual.

In a second aspect of the invention there is provided a method for diagnosing cystic fibrosis in an individual comprising the steps of:
obtaining a biological sample from the individual;
isolating nucleic acids from the sample; and
testing the biological sample for the presence of one or more nucleic acid sequences, fully complementary to one or more segments of the CFTR gene, wherein said one or more nucleic acid sequences correspond to the mutation to be identified and may be selected from the group comprising SEQ IDs: 1-3.

According to a third aspect of the invention there is provided a method for determining if an individual or the individual's offspring will have a predisposition to CF, the method comprising the steps of:
obtaining a biological sample from the individual;
isolating nucleic acids from the sample;
testing the biological sample for the presence of one or more nucleic acid sequences, fully complementary to one or more segments of the CFTR gene, wherein said one or more nucleic acid sequences correspond to the mutation to be identified and may be selected from the group comprising SEQ IDs: 1-3; and
determining from the test results if the individual or the individual's offspring has a predisposition for CF, and advising the individual accordingly.

According to a fourth aspect of the invention there is provided a kit for performing one or more of the methods according to the invention. In particular, the kit may be provided with primers and probes required to detect the presence of nucleic acids using the detection methods in accordance with one or more of the aspects of the invention.

According to a fifth aspect of the invention there is provided one or more nucleic acid sequences, fully complementary to one or more segments of the CFTR gene, wherein said one or more nucleic acid sequences correspond to the mutation to be identified and may be selected from the group comprising SEQ IDs: 1-3.

Further according to any of the aspects according to the invention, the invention can be used to detect CF, but also CF related diseases or other monogenic disorders.

Further according to any of the aspects according to the invention, the invention may be used in the detection of complex alleles consisting of two or more CFTR gene mutations.

DESCRIPTION OF PREFERRED
EMBODIMENTS OF THE INVENTION

In accordance with the invention, cystic fibrosis transmembrane conductance regulator (CFTR) gene mutations are identified by a plurality of steps.

DNA Isolation

In a first step, one or more isolated purified nucleic acids each comprising 25 nucleotides occurring in the CFTR DNA, the nucleic acids being fully complementary to one or more segments of the CFTR gene, are selected from the group of CFTR gene mutations comprising c.1277_1278insAT, c.3512_3516dupCAGAA or c.2630delC.

Blood samples are collected from patients that are believed to be suffering from CF, and DNA is isolated from the blood of the patients, whereafter the presence of one or more of the CFTR gene mutations in the DNA is determined using a suitable detection method.

The protocol for extracting the DNA from the blood samples is initiated once the white blood cell count (WBCC) for a particular patient is determined, which usually occurs within 24 hours of a patient giving a blood sample. A maximum of $2 \times 10^7$ white blood cells are recommended per column for spin-column based nucleic acid purification (in this embodiment, the QIAGEN column is used). Samples containing more than this can be diluted using 1× phosphate buffered saline (PBS) and equal volumes applied to two separate columns.

In this embodiment, QIAGEN protease (200 μL) is then placed in the bottom of a 15 mL centrifuge tube, 2 mL of blood added and the tube subjected to a brief vortexing step to ensure thorough mixing. Buffer AL (2.4 mL) is added to the mixture, the tube inverted 15 times and then shaken vigorously by hand for 1 minute, before being incubated at 70° C. for 10 minutes. The tube is removed, 2 mL of molecular biology grade absolute ethanol added, the tube inverted 10 times and shaken vigorously by hand for a minute. Half of the solution is transferred to a QIAamp Midi column in a 15 mL centrifuge tube without moistening the rim. The tube is spun at 1850 g for 3 minutes, the column removed, the filtrate discarded, the remainder of the solution applied to the column and the centrifugation step repeated. Without touching the rim of the column, 2 mL of Buffer AW1 is added and the closed tube spun at 4500 g for 1 minute. Again without moistening the rim, 2 mL Buffer AW2 is added, the tube closed and spun at 4500 g for 15 minutes. The filtrate is discarded, the column placed in a new 15 mL tube and 300 μL room temperature Buffer AE added to the centre of the column. The tube is then incubated at room temperature for 5 minutes and spun at 4500 g for 2 minutes. The resulting eluate is removed from the tube, placed in the centre of the column and the procedure repeated to obtain a more concentrated first eluate. The column is then placed in a new 15 mL tube, an additional 300 μL room temperature Buffer AE added to the centre of the column and the elution steps above repeated to obtain a second eluate.

A spectrophotometer (such as the NanoDrop spectrophotometer) is used for DNA quantification purposes. A 1:10 dilution of the first eluate is made using water as the diluent; the second eluate is then read undiluted. Buffer AE (2 μL) is used as the blank. The instrument is re-blanked after every three to four readings, and each sample is measured using 2 μL of either the diluted (first eluate) or undiluted (second eluate) DNA.

Each eluate (5 μL) is then visualised on a 0.7% agarose gel electrophoresed in 1XTBE (tris-borate-EDTA), stained with nucleic acid stain (such as Biotium GelRed) diluted 1:16,667 times in 50 mL of molten agarose. The DNA is then subjected to electrophoresis at 90 V of current using Lab Aid Mass Ruler High Range as the molecular ladder.

Mutation Detection

Suitable detection methods for determining the presence of CFTR gene mutations include the amplification refractory mutation system (ARMS), next generation sequencing (NGS), quantitative polymerase chain reaction (qPCR) and microarrays.

The amplification refractory mutation system (ARMS) can be used in diagnosing various diseases including cystic fibrosis (CF). Whereas ARMS requires separate reactions to identify the mutant and the wildtype sequences, tetra-primer ARMS allows for the identification of both mutant and wildtype in the same reaction tube relying on the use of four primers. The first primer pair are the outer flanking primers which are based on the wildtype sequence and there is a second pair of inner primers. The forward inner primer is specific to the wildtype sequence whereas the reverse inner primer is specific to the mutant sequence (Ye et al., 2001; Ye et al 1992). This methodology can be used to identify the mutations discovered in CF patients in general, but more particularly in non-white CF patients, with the relevant primers, corresponding to SEQ ID: 4-15, being listed in table 1. In addition to these primers, the reaction requires a suitable PCR reaction buffer, Taq DNA polymerase, deoxyribose nucleoside triphosphates (dNTP's), nuclease-free water, and the patient DNA. This is subjected to either an amplification program involving five cycles at the annealing temperature of the flanking primers, followed by 30 cycles at the annealing temperature suitable for the inner primers or a touchdown PCR with the initial annealing temperature being 72° C., decreasing by 1° C. per cycle until the temperature of the inner primers is reached and continuing at that temperature until the end of the PCR programme. The general programme also has an initial denaturation step at 95° C. for 1 minute. The amplification step consists of 35 cycles of 95° C. for one minute, one minute at the previously described annealing temperature and one minute at 72° C. There will be a final extension step at 72° C. for three minutes. The amplicons are then resolved on a 1% agarose gel. The expected amplicon sizes are also listed in table 1.

In accordance with the invention, next generation sequencing (NGS) could also be used to identify the CF mutations in a sample of patient DNA. Probes specific to these mutations are used to assist in diagnosing patients carrying these variants. A pair of probes, one annealing upstream of the mutation and the other annealing downstream, is needed per mutation. A DNA polymerase is used to fill in the gap between the probes with complementary dNTPs. Ligase is then used to join the neighbouring bases, resulting in a complete double stranded molecule. Once double-stranded DNA has been produced by these processes, PCR is used to add sequencing primers and indices to the construct. The library of DNA fragments bound to the probes are then ready for NGS, which is an automated process. The applicable probes, corresponding to SEQ ID: 16-21, are listed in table 2.

TABLE 1

The tetra-ARMS primers for identification of CF mutations.

| Mutation | Primers | Annealing Temperature/ ° C. | Amplicon size/bp |
| --- | --- | --- | --- |
| SEQ ID: 1 | ACAATAGAAAAACTTCTAAT GGTGATAAC (fi) (SEQ ID NO: 4) | 58.66 | Wt: 409 Mt: 223 |
|  | GAGAAATTACTGAAGAAGA GGCTGATT (ri) (SEQ ID NO: 5) | 60.89 |  |
|  | CAGTGTAATGGATCATGGG CCATGTGCT (fo) (SEQ ID NO: 6) | 72.66 |  |
|  | GCTCGCCATGTGCAAGATA CAGTGTTG (ro) (SEQ ID NO: 7) | 70.8 |  |
| SEQ ID: 2 | CCATTCCAGGTGGCTGCCT C (fi) (SEQ ID NO: 8) | 64.82 | Wt: 345 Mt: 188 |
|  | GGAGCCACAGCACAACCAC AA (ri) (SEQ ID NO: 9) | 63.92 |  |
|  | CTGCTGGACCCAGGAACAA AGCAAAGG (fo) (SEQ ID NO: 10) | 73.65 |  |
|  | CACTATATTGTCCAGGCTGG AGTGCGGTG (ro) (SEQ ID NO: 11) | 73.4 |  |
| SEQ ID: 3 | TTCATTGACATGCCAACAGT AG (fi) (SEQ ID NO: 12) | 56.25 | Wt: 299 Mt: 447 |
|  | GGTAGGTTTACCTTCTGTTC TGTT (ri) (SEQ ID NO: 13) | 56.23 |  |
|  | GAATCTTCAGTAGTGGTTTT GAGGTGTGG (fo) (SEQ ID NO: 14) | 66.99 |  |
|  | TGCTAACACATTGCTCAGGC TACTGGG (ro) (SEQ ID NO: 15) | 69.74 |  |

Fi = forward inner; fo = forward outer; ro = reverse outer; ri = reverse inner; wt = wildtype; mt = mutant

TABLE 2

Probes that are used to identify CFTR mutations via NGS.

| Mutation | Upstream Probe | Downstream Probe |
| --- | --- | --- |
| SEQ ID: 1 | GTGTGTTTTTTTAACAGGGA TTTGGGGAAT (SEQ ID NO: 16) | GGATCCAGCAACCGCCAACAACTG (SEQ ID NO: 17) |
| SEQ ID: 2 | ATGTGAATTTAGATGTGGGC ATGGGAG (SEQ ID NO: 18) | TCTTTCCACTACCATAATGCTTGGGA G (SEQ ID NO: 19) |
| SEQ ID: 3 | GCCCGACAAATAACCAAGT GACAAATAGC (SEQ ID NO: 20) | AGGGCCAGATGTCATCTTTCTTCACG (SEQ ID NO: 21) |

Quantitative PCR (qPCR) is an analytical technique that allows the real-time tracking of the process of amplification. qPCR hybprobes, in conjunction with qPCR primers, can be used to ascertain if the mutations described are in fact present in a sample of human DNA. The necessary primers and probes, corresponding to SEQ ID: 22-33, are listed in table 3. In addition to the primer and probe pairs, the reaction also needs to include an appropriate qPCR master mix and about 250 ng of template DNA. The probes are labelled with the fluorophores listed in order to allow for detection of the mutations, if present, while the amplification is proceeding. The reactions could be further optimised to allow for multiplexing to enable all three mutations to be assayed for simultaneously in one reaction vessel. The amplification programme consists of one cycle at 94° C. for 3 minutes, thirty cycles of 94° C. for 30 seconds, 55° C. for 30 seconds and 72° C. for 30 seconds. The fluorescence is then captured at the annealing step. After the completion of the amplification, a melt curve analysis is used to distinguish between the wildtype and mutant sequences. This is executed by heating the reaction tubes to 95° C. for 30 seconds, lowering the temperature to 45° C. and then raising the temperature to 95° C. in 0.1° C. increments with fluorescence being continuously captured as the temperature is increased.

Microarrays are based on the principle of hybridisation. DNA fragments (probes) are attached to a solid substrate (such as a chip) and immobilised. Nucleic acid from a relevant source is denatured, labelled and allowed to incubate with the probes at an appropriate temperature overnight. The substrate is then washed to remove unbound DNA and the formation of bonds between the probes and the target DNA detected using a method appropriate for the label that is used in the beginning of the protocol. Probes that could be used as part of a microarray screening for CF-associated mutations, corresponding to SEQ ID: 34-36 are listed in table 4. The genomic DNA is denatured, snap cooled on ice and labelled dNTPs and Klenow fragments used to incorporate labels into the sequence. The labelled DNA is purified using a PCR purification kit such as the QIAQuick PCR purification kit. The hybridisation and visualisation protocol for the commercially available microarray selected is followed, and involves a pre-hybridisation step involving a buffer and the chip at a suitable temperature. The labelled DNA is then introduced to the microarray chip and incubated overnight at the pre-hybridisation temperature. The chip is washed using solutions containing SDS (sodium

TABLE 3 qPCR primers and probes utilised to identify CFTR gene mutations in human DNA samples

| Mutation | qPCR Primers | Hybprobes |
| --- | --- | --- |
| SEQ ID: 1 | F: ATGGGCCATGTGCTTTTCAAAC (SEQ ID NO: 22) R: GCAACCGCCAACAACTGTCC (SEQ ID NO: 23) | TGATGAATCAGCCTCTTCTTCAGTAA TTTCTC-Fluroscein (SEQ ID NO: 28) Texas Red- ACTTCTTGGTACTCCTGTCCTGAAAG ATATTAATT-PHO (SEQ ID NO: 29) |
| SEQ ID: 2 | F: TAGATGTGGGCATGGGAGGA (SEQ ID NO: 24) R: CCACTACCATAATGCTTGGGAGA (SEQ ID NO: 25) | TTTTTGGTTGTGCTGTGGCTCCTT- Fluorescein (SEQ ID NO: 30) Cy5- GGAAAGTGAGTATTCCATGTCCTATT GTGTAG-PHO (SEQ ID NO: 31) |
| SEQ ID: 3 | F: GCCCGACAAATAACCAAGTGAC (SEQ ID NO: 26) R: ACAGTCATTTGGCCCCCTG (SEQ ID NO: 27) | GCCAACAGAACAGAAGGTAAACCTA CCAAGT-Fluorescein (SEQ ID NO: 32) LCRed640- CAACCAAACCATACAAGAATGGCCA AC-PHO (SEQ ID NO: 33) |

PHO = phosphorylated 3' end dodecyl sulphate) and SSC (sodium citrate and sodium chloride, pH 7). Hybridisation is detected as prescribed for the system used.

TABLE 4

The microarray probes for CF mutation detection

| Mutation | Microarray Probe |
|---|---|
| SEQ ID: 1 | ATGGTGATGAATCAGCCTCTTCTTC (SEQ ID NO: 34) |
| SEQ ID: 2 | AGGTGGCTGCTTTTTGGTTGTGCTG (SEQ ID NO: 35) |
| SEQ ID: 3 | ACATGCCAACAGAACAGAAGGTAAA (SEQ ID NO: 36) |

Bioinformatics Pipeline for the Detection of Variants in Human DNA

The initial analyses (including base calling and extracting cluster intensities) are conducted using real-time analysis software suite, such as Illumina MiSeq RTA 1.14.23. Here a sequence quality filtering script is executed using Illumina CASAVA version 1.8.2. Data analysis is conducted in four stages. In the first stage, CASAVA's variant calls are assessed for novelty and potential functional consequences using suitable analysis approaches, as known in the art. Here the online Variant Effect Predictor tool (http://www.ensembl.org/info/docs/tools/vep/index.html) from Ensembl is used. This tool is asked to return SIFT and PolyPhen scores as well as co-located variations and information, if available, about each variant present in the 1000 Genomes Project.

Second, the raw sequence files are imported into a suitable genomic analysis software suite where they are assessed for quality. Sections of the sequence that fall below a quality score of 20 are trimmed, as are any remaining adapter sequences identified. The reads are mapped to chromosome seven and CFTR (version hg19; both obtainable from the online UCSC Genome browser database: http://hgdownload.soe.ucsc.edu/downloads.html) and quality based variant detection used to identify differences between the reads and the reference sequences. Only variants present in both forward and reverse reads are returned. The variants called after being mapped to CFTR are annotated with exon number, possible changes to the amino acid sequence and possible splice site effects; those called after being mapped to chromosome seven are annotated from known dbSNP variants and with conservation scores based on the chromosome seven PhastCons wiggle file obtained from the UCSC Genome browser. Potential structural variants and indels are also identified.

Third, a bioinformatics pipeline is constructed using existing bioinformatics approaches as known in the art. The raw files are assessed for quality and sections of sequence with a quality score less than 20 are trimmed. The trimmed (as needed) raw sequence data, the *.vcf files from both CASAVA and the CLC Genomics Workbench processes, the dbSNP database, the Mills and 1000 Genomes known indels database, the CFTR sequence and the human genome (version hg19) are used as input data in the bioinformatics pipeline. A sequence alignment tool, as known in the art, is used to map the reads to the human genome, while statistical approaches, as known in the art, are used to report on the statistics of the mapping (such as the percentage of reads mapped to the reference). Any alignment discrepancies generated by the presence of indels are located and these errors fixed. The quality scores for each read position are then corrected, taking into account errors inherent in the NGS technology while preserving biologically known variants. Genotyping tools and approaches, as known in the art, are used to call variants, which are then filtered and annotated. The output of the bioinformatics pipeline thus contains an annotated list of variants identified by the various software tools used during the analysis. This analysis is done for each participant and the data exported as separate files.

All the variants from all the study participants are copied into one spreadsheet. Conditional formatting is used to identify the duplicate variants which are removed. These unique calls are manually edited to the input format required for additional annotation. The data returned after annotation is downloaded into a spreadsheet and the variants filtered by consequence. The data must be closely examined, paying particular attention to whether or not the variant has already been identified, whether or not the global minor allele frequency and the minor allele frequency per population is ≤1% (infrequent CFTR variants are more likely to be associated with pathology; Raynal et al., 2013; Bombieri et al., 2000), which exon or intron it is located in, whether or not its clinical significance is known, and its HGVSc and HGVSp notations. Exonic variants are additionally examined for their SIFT and PolyPhen scores. They may also assessed by means of further software tools designed to facilitate integration of computational tool output. Here the software tool Condel (González-Pérez and López-Bigas 2011) is used. Condel takes the weighted average of the normalised scores of five in silico predictive tools (including SIFT and PolyPhen) resulting in a greater degree of accuracy. All the intronic variants are formatted as required before being uploaded to the online software tool RegulomeDB (http://regulome.stanford.edu/; Boyle et al, 2012) which utilises ENCODE and other data to rank intronic variants by their likely impact on transcription and gene regulation. Variants which are identified as having an impact on the splice sites of the CFTR gene are subject to additional analyses using the software tools Human Splicing Finder 2.4.1 (http://www.umd.be/HSF/HSF.html; Desmet et al 2009) and SpliceAid2 (http://193.206.120.249/splicing_tissue.html; Piva et al 2012). Additionally, all identified variants must be checked against the CFTR2 database (Sosnay et al, 2013; http://cftr2.org/mutations_history.php) in order to find out if their functional significance has already been empirically determined. These data, in addition to the patient's clinical file, are used to determine which variants might be potentially pathogenic.

Fourth, programs are used to provide a level of in silico validation of the aligned files respectively. Here pibase (Forster et al., 2013) and BAYSIC (Cantarel et al., 2014) are used. Since both programs were written for use in a command line environment, the operating system ubuntu 12.04 (Precise Pangolin) is installed. The programming languages Python 2.7.3 and pysam 0.6 are installed as pre-requisites for using pibase. The Python path is exported before using pibase every time a new terminal is opened. A file generated by the bioinformatics pipeline is sorted, MD-tagged and indexed. From within the pibase directory, data is extracted from this file at positions specified by the file output generated by the bioinformatics pipeline using all the variant calling programs. The command defaults are used except the read length, which for the current data is 150 bp; the chromosome naming convention used in the files need to be identical. A script is used to determine what the best genotype at the positions of interest are. Since pibase ignores indels, any position of interest where more than three reads are ignored is examined using a genome visualisation tool, as known in the art, to allow for manual inspection of the region of interest.

The Tabix and vcftools are compiled from within the BAYSIC directory. The posterior probability for each variant called by the variant callers is calculated from the BAYSIC directory using the correct commands, with the names of the input files which are downloaded from the bioinformatics pipeline before the filtering and annotation steps.

Conclusion

Resolving a patient's molecular diagnosis in this way would also be useful in designing a genetic test with a higher mutation detection rate and in deciding if a patient may benefit from CF class specific drugs. This should prove especially useful for populations with high genetic diversity, such as individuals of African descent, which have suffered from the inherent European bias in the current genetic tests. Sequencing coupled with an appropriate public health policy could lower the age at diagnosis for CF patients which should both decrease morbidity and raise life expectancy. This unbiased approach would assist in gradually eliminating the immediate diagnostic disadvantage faced by non-Caucasian CF patients.

It is accordingly asserted that the disadvantages associated with known methodologies and diagnostic practices for determining and confirming a diagnosis of CF, and in particular in individuals of African or mixed race origin, could be alleviated with the methodology and kit according to the invention.

In particular, the disadvantage of having to rely solely on known diagnostic methods, including the so called classic triad of symptoms, is overcome by providing a molecular basis for determining and/or confirming a diagnosis of CF in patients of African or mixed race origin, where this molecular basis had not previously been available.

The disadvantage of a diagnostic bias existing in favour of the molecular diagnosis of CF in Caucasian patients is alleviated by the method and kit according to the invention providing a viable molecular diagnosis of CF in patients of African or mixed race origin by the utilisation of a method to identify CFTR gene mutations that have not previously been documented, and which mutations are evident in patients of African and mixed race origin.

Accordingly, the perceived and internationally prevalent misconception that patients of African or mixed race origin are not susceptible to CF is disproven in accordance with the invention, which should ultimately benefit African or mixed race individuals that suffer from CF. It will further increase the overall positive diagnosis of CF in individuals of any origin, in view of the methodology according to the invention being focused on but not limited to CF patients of African and mixed race origin, and accordingly includes any other patients presenting the CFTR gene mutations described herein.

It will be appreciated that in terms of the invention, variations in details are possible without departing from the scope of this disclosure and the appended claims.

The invention claimed is:

1. A method of detecting the presence of a mutation in a cystic fibrosis transmembrane conductance regulator (CFTR) gene of an individual, including the steps of:
   providing a labeled nucleic acid sequence comprising SEQ ID NO: 32;
   providing a biological sample of the individual to be tested for CF;
   isolating nucleic acids from the biological sample;
   contacting the nucleic acid of the sample with the labeled nucleic acid sequence; and
   detecting the label; wherein the presence of the label indicates the presence of the mutation in the CFTR gene in the sample of the individual.

2. The method of detecting the presence of a mutation in the CFTR gene of an individual according to claim 1, wherein the detection method utilizes quantitative polymerase chain reaction (qPCR).

3. The method of claim 1, further comprising detecting the presence of the mutation in the CFTR gene in the sample of the individual using a ARMS detection method and one or more tetra-ARMS primers selected from the group consisting of SEQ ID NOs: 12-15.

4. The method of claim 1, further comprising detecting the presence of the mutation in the CFTR gene in the sample of the individual using a NGS detection method and one or more probes selected from the group consisting of SEQ ID NOs: 20-21.

5. The method of detecting the presence of a mutation in the CFTR gene of an individual according to claim 2, wherein the qPCR detection method comprises contacting the nucleic acid of the sample with one or more primers selected from the group consisting of SEQ ID NOs: 26-27, and optionally, contacting the nucleic acid of the sample with a second labeled nucleic acid sequence comprising SEQ ID NO: 33.

6. The method of claim 1, further comprising detecting the presence of the mutation in the CFTR gene in the sample of the individual using a microarray detection method and SEQ ID NO: 36 as a probe.

7. The method according to claim 1, wherein the individual is of African origin.

8. The method according to claim 1, wherein the biological sample contains DNA.

9. The method according to claim 8, wherein the biological sample is obtained from the individual's blood, serum, plasma, urine, skin, or hair.

10. A method for diagnosing cystic fibrosis (CF) in an individual comprising the steps of:
    obtaining a biological sample from the individual;
    isolating nucleic acids from the sample;
    providing a labeled nucleic acid sequence comprising SEQ ID NO: 32;
    contacting the nucleic acid of the sample with the labeled nucleic acid sequence;
    detecting the label; wherein the presence of the label indicates the presence of the mutation in the CFTR gene in the sample; and
    diagnosing CF in the individual when the mutation is present.

11. The method according to claim 10, wherein the individual is of African origin.

12. The method according to claim 10, wherein the biological sample contains DNA.

13. The method according to claim 12, wherein the biological sample is any sample obtained from the individual's blood, serum, plasma, urine, skin, or hair.

14. The method according to claim 10, wherein the method further comprises contacting the nucleic acid of the sample with one or more primers selected from the group consisting of SEQ ID NOs: 26-27, and optionally, contacting the nucleic acid of the sample with a second labeled nucleic acid sequence comprising SEQ ID NO: 33.

15. A method for determining if an individual or the individual's offspring will have a predisposition to CF, the method comprising the steps of:
    obtaining a biological sample from the individual;
    isolating nucleic acids from the sample;
    providing a labeled nucleic acid sequence comprising SEQ ID NO: 32;
    contacting the nucleic acid of the sample with the labeled nucleic acid sequence;
    detecting the label; wherein the presence of the label indicates the presence of the mutation in the CFTR gene in the sample; and
    advising the individual that the individual or the individual's offspring will have a predisposition to CF when the mutation is present.

16. The method according to claim 15, wherein the individual is of African origin.

17. The method according to claim 15, wherein the biological sample contains DNA.

18. The method according to claim 17, wherein the biological sample is obtained from the individual's blood, serum, plasma, urine, skin, or hair.

19. The method according to claim 15, wherein the method further comprises contacting the nucleic acid of the sample with one or more primers selected from the group consisting of SEQ ID NOs: 26-27, and optionally, contacting the nucleic acid of the sample with a second labeled nucleic acid sequence comprising SEQ ID NO: 33.

20. A kit for identifying mutations in the CFTR gene of an individual, wherein the kit is provided with primers selected from the group consisting of SEQ ID NOs: 26-27, a labeled probes comprising SEQ ID NO: 32, and optionally, a second labeled probe comprising SEQ ID NO: 33.

* * * * *